US00PP17208P2

(12) United States Plant Patent
Egger

(10) Patent No.: US PP17,208 P2
(45) Date of Patent: Nov. 14, 2006

(54) ***HEUCHERA* PLANT NAMED 'SPARKLING BURGUNDY'**

(50) Latin Name: *Heuchera hybrid*
Varietal Denomination: Sparkling Burgundy

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 45 days.

(21) Appl. No.: 11/165,707

(22) Filed: Jun. 24, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct hybrid of *Heuchera* plant characterized by to burgundy colored foliage, white flowers on short, burgundy flowering stems, mounding habit, and excellent vigor.

1 Drawing Sheet

Botanical denomination: *Heuchera* hybrid.
Variety designation: 'Sparkling Burgundy'.
Cross Reference to sibling: *Heuchera* 'Peach Flambé' (U.S. Plant patent application Ser. No. 11/154,434).

The present invention relates to a new and distinct cultivar of *Heuchera* and given the cultivar name of 'Sparkling Burgundy'. *Heuchera* is in the family Saxifragaceae. *Heuchera* 'Sparkling Burgundy' originated from a cross between *Heuchera* H-01-dklf-6 (an unpatented, proprietary plant) as the seed parent, and *Heuchera* 'Amber Waves' (U.S. Plant Pat. No. 13,348) as the pollen parent. Given its ornamental foliage and flower form, it is probable that *Heuchera micrantha, H. americana,* and *H. brizoides* are in its parentage.

This new *Heuchera* is distinguished by:

1. Unique burgundy colored foliage.
2. White flowers on dark peduncles.
3. Mounding habit.
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
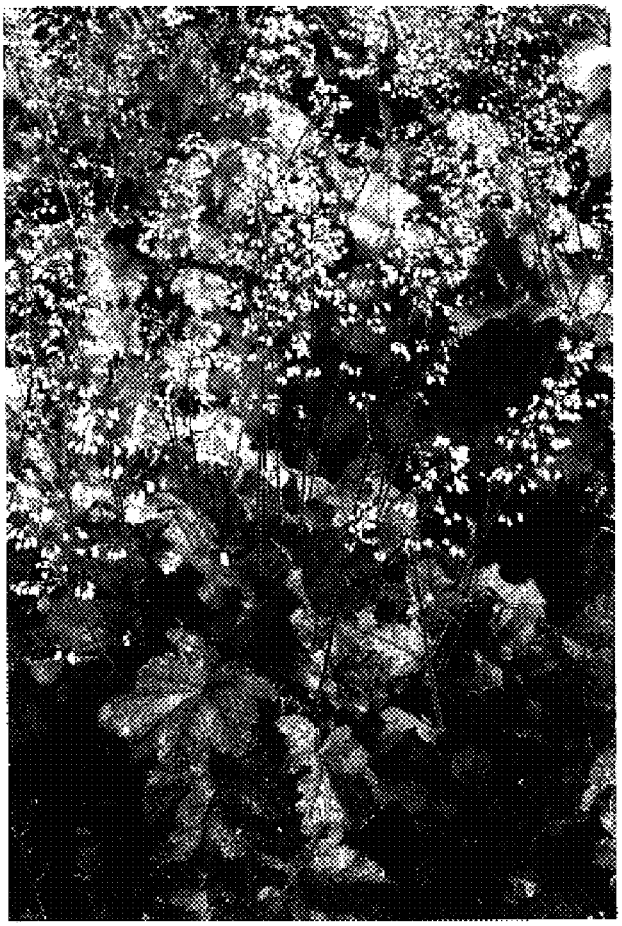
FIG. 1 shows a two year old plant of *Heuchera* 'Sparkling Burgundy' in flower in May growing in the ground in the shade garden in Canby, Oreg.
Figure 2:
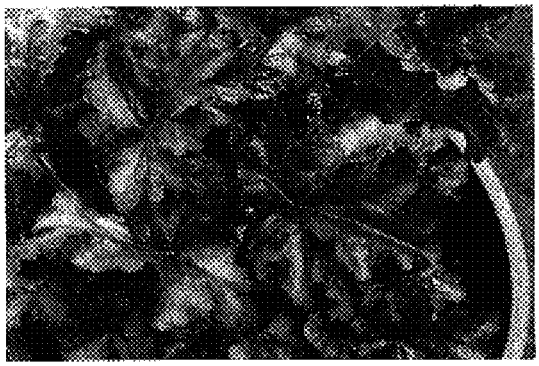
FIG. 2 shows a three-year-old plant growing in a five gallon container in the shade house in April.
Figure 3:
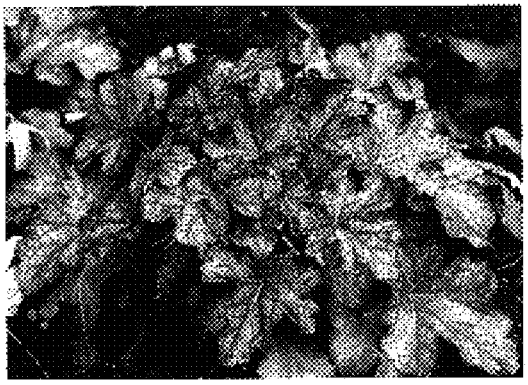
FIG. 3 shows a two year old plant growing in the ground in the garden in October.

The following is a detailed description of the new *Heuchera* cultivar based on observations taken in May of a three-year-old specimen grown a five gallon container in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Botanical denomination: *Heuchera* hybrid.
Variety designation: 'Sparkling Burgundy'.
Parentage: *Heuchera* H-01-dklf-6 (seed parent, proprietary, unreleased plant)×*Heuchera* 'Amber Waves' (U.S. Plant Pat. No. 13,348 (pollen parent).

Plant:
- *Form.*—Basal rosette, herbaceous perennial.
- *Hardiness.*—USDA Zone 4 to 9.
- *Size.*—30 cm tall from the soil to the top of the foliage and 55 cm wide.
- *Habit.*—Mounding.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Ovate.
- *Lobing/division.*—5 main lobes, with 1 to 2 shallow secondary lobes.
- *Venation.*—Palmate.
- *Margins.*—Crenate.
- *Apex.*—Mucronulate.
- *Base.*—Cordate, lobes slightly overlapping at the base.
- *Blade size.*—8 to 12 cm long and 8 to 12.5 cm wide.
- *Surface texture.*—Glandular on both sides.
- *Petiole description.*—15 to 19 cm long and 2 mm wide, glandular, Red Purple 59A.

*Leaf color.*—Spring and summer topside — Burgundy with a silver pink veil, Greyed Purple 187A with Red Purple 69A. Bottom side all seasons — Grayed Purple 187C and D. Winter topside — Between Greyed Purple 183A and Brown 200C with a veil of Red Purple 69A.

Inflorescence:

*Type.*—Thyrse.

*Number of flowers.*—90 per thyrse.

*Number of thyrse.*—17 in spring.

*Peduncle.*—With 0 to 2 petiolate cauline leaves (ovate, blades grow to 7 cm long and 5.5 cm wide and are incised at base and crenate), 48 cm tall and 4 mm wide near the base, with glandular hairs, Greyed Purple 187A to 187B.

*Pedicel.*—Variable in size, with glandular hairs, Grayed Purple 187A.

*Bloom period.*—May in Canby, Oreg.

Flower bud:

*Size.*—2.5 mm wide and 4 mm long.

*Description.*—Glandular, ovoid.

*Color.*—Dull white, Yellow White 158A.

Flower:

*Type.*—Perfect, zygomorphic.

*Shape.*—Campanulate.

*Size.*—6 mm long and 3.5 mm wide.

*Petal description.*—5 in number, inconspicuous, 2 mm long, spatulate with a clawed base, margin entire, apex acute, White 155D on both sides, backs glandular.

*Calyx description.*—5 mm long and 3.5 mm wide, with 5 lobes, divided ¼ way to the base, glandular on backs only, margins entire, lobe apices acute, Yellow White 158B to White 155A on both sides.

*Stamen description.*—5, sterile, no pollen produced, Yellow White 158A overall, filaments 1.5 mm long, anthers 0.4 mm long.

*Pistil description.*—Yellow White 158A overall, 3.5 mm long, style 1.5 mm long.

*Fragrance.*—None.

*Lastingness.*—Each thyrse blooms for about 2 weeks on the plant.

Fruit:

*Type.*—Two-beaked ovoid capsule.

*Color.*—Brown 200D.

Seed:

*Shape.*—Linear.

*Size.*—2 mm long.

*Color.*—Black, RHS 202A.

Pest and disease tolerance: Excellent disease resistance to powdery mildew, the common problem of *Heuchera*. Susceptible to *Heuchera* rust and root weevils.

COMPARISON TO SIMILAR *HEUCHERAS*

Compared to purple leaf *Heuchera* on the market this new variety has pinker leaves and larger flowers on shorter burgundy stalks.

Compared to *Heuchera* 'Amber Waves', the pollen parent, the new variety is larger and more vigorous, with larger, unruffled leaves, and burgundy rather than amber foliage color.

Compared to *Heuchera* H-01-dklf-6, the seed parent, the new variety has burgundy rather than brown leaves and white rather than warm pink flowers.

I claim:

1. A new and distinct hybrid of *Heuchera* plant as herein illustrated and described.

* * * * *